United States Patent [19]

Desarzens et al.

[11] Patent Number: 5,502,396
[45] Date of Patent: Mar. 26, 1996

[54] MEASURING DEVICE WITH CONNECTION FOR A REMOVABLE SENSOR

[75] Inventors: Pierre Desarzens, Bienne; Rudolf Dinger, St-Aubin, both of Switzerland

[73] Assignee: Asulab S.A., Bienne, Switzerland

[21] Appl. No.: 309,778

[22] Filed: Sep. 21, 1994

[30] Foreign Application Priority Data

Sep. 21, 1993 [FR] France .................. 93 11318

[51] Int. Cl.⁶ .................................. G01N 27/26
[52] U.S. Cl. .................. 324/713; 324/718; 324/756; 324/715; 340/686; 204/403; 204/406
[58] Field of Search .................... 324/713, 715, 324/718, 754, 756, 757, 133, 538, 555; 340/686, 687; 204/403, 406, 153.12

[56] References Cited

U.S. PATENT DOCUMENTS

| | | | |
|---|---|---|---|
| 4,225,819 | 9/1980 | Grau et al. | 324/754 |
| 5,115,200 | 5/1992 | Lahitte et al. | 324/718 |
| 5,282,950 | 2/1994 | Dietz et al. | 204/406 |
| 5,366,609 | 11/1994 | White et al. | 204/406 X |
| 5,395,504 | 3/1995 | Saurer et al. | 204/403 |

FOREIGN PATENT DOCUMENTS

| | | |
|---|---|---|
| 121385 | 10/1984 | European Pat. Off. . |
| 429076 | 5/1991 | European Pat. Off. . |
| 523463 | 1/1993 | European Pat. Off. . |
| WO9010861 | 9/1990 | WIPO . |
| WO9100998 | 1/1991 | WIPO . |
| WO9304371 | 3/1993 | WIPO . |

*Primary Examiner*—Kenneth A. Wieder
*Assistant Examiner*—Diep Do
*Attorney, Agent, or Firm*—Sughrue, Mion, Zinn, Macpeak & Seas

[57] ABSTRACT

The present invention concerns a measuring device, notably for measuring the level of glucose in blood, intended to be used with a removable sensor comprising at least one active zone. In particular, the invention concerns the electrical connection between the measuring device and the removable sensor. Each electrical contact surface of the removable sensor is connected to two electrical contact organs to enable the condition of the electrical contacts between these electrical contact organs and the corresponding contact surfaces to be checked before a measurement is carried out.

13 Claims, 3 Drawing Sheets

MEASURING DEVICE WITH CONNECTION FOR A REMOVABLE SENSOR

FIELD OF THE INVENTION

The present invention concerns a measuring device intended to be used with a removable sensor. For example, such a measuring device is used to carry out measurement of the electrochemical type, in particular to measure the glucose level in blood. The electrochemical functioning of such a measurement is described for example in patent application WO 92/14 836.

More particularly, the present invention concerns the electrical connection between such a measuring device and a removable sensor used with this measuring device.

FIG. 1 shows a schematical general view of a measuring device, designated by the general reference 2, and a removable sensor designated by the reference 4.

Removable sensor 4 comprises an active zone 6 and two contact surfaces 8 and 10 electrically connected to active zone 6 via two conductors which are not shown.

BACKGROUND OF THE INVENTION

FIG. 2 shows a schematical view of a conventional electrical connection between a measuring device (partially shown) and a removable sensor of the type shown in FIG. 1.

The electrical connection is realised by two metallic strips connected respectively to the two contact surfaces 8 and 10, the latter being electrically connected in series to active zone 6 of removable sensor 4.

In order to enable removable sensor 4 to be introduced into the measuring device or to be withdrawn from the latter, the electrical connection is ensured only by pressure from metallic strips 12 and 14 on the respective contact surfaces 8 and 10, these strips 12 and 14 exhibiting a certain elasticity.

The electrical connection arrangement described above is not very reliable. Indeed, it can easily happen than one of the metallic strips becomes distorted following the repeated introduction of removable sensors or that the pressure exercised by the metallic strip is insufficient to establish a proper electrical connection. Further, removable sensor 4 may be defective and the contact surfaces may have, for example, an abnormal electrical resistance.

The different problems cited above are especially disastrous for measurements of a medical nature.

SUMMARY OF THE INVENTION

A purpose of the present invention is to overcome the lack of security of the electrical connection between a measuring device and a removable sensor intended to be used with this measuring device.

The present invention therefore concerns a measuring device intended to be used with a removable sensor having at least two electrical contact surfaces, this measuring device comprising measuring means and connection means comprising at least two first contact means. These two first contact means are used respectively to establish an electrical connection between the two contact surfaces of said removable sensor and the measuring means. This measuring device is characterized in that said connection means also comprises two second contact means, the two second contact means being used respectively to connect electrically the two contact surfaces of said removable sensor to testing means enabling said electrical connection between each of the two first contact surfaces and said measuring means to be tested.

The doubling of contact means according to the invention between the measuring device and the removable sensor with which it is used enables, according to different embodiments, at least one electric circuit to be established, not including the active zone of the removable sensor, and enables one to test whether the electrical connection between the first contact means and the respective contact surfaces of said removable sensor is correctly established, to the extent that the electrical connection between the second contact means and the respective electrical contact surfaces of said removable sensor is also correctly established.

It is therefore possible, before carrying out a measurement by the intermediary of the measuring device and the removable sensor with which it is used, to ensure that the establishment of an electrical connection between each of the first or second contact means intervening in the measurement and the removable sensor is correctly established.

According to another characteristic of the invention, it is also possible to test whether the sensor used for measuring is defective.

BRIEF DESCRIPTION OF THE DRAWING

Other advantages and characteristics of the invention will become clear with the help of the following description made with reference to the attached drawings, given purely by way of a non-limiting example, in which.

DESCRIPTION OF THE PREFERRED EMBODIMENTS

Figure 1:
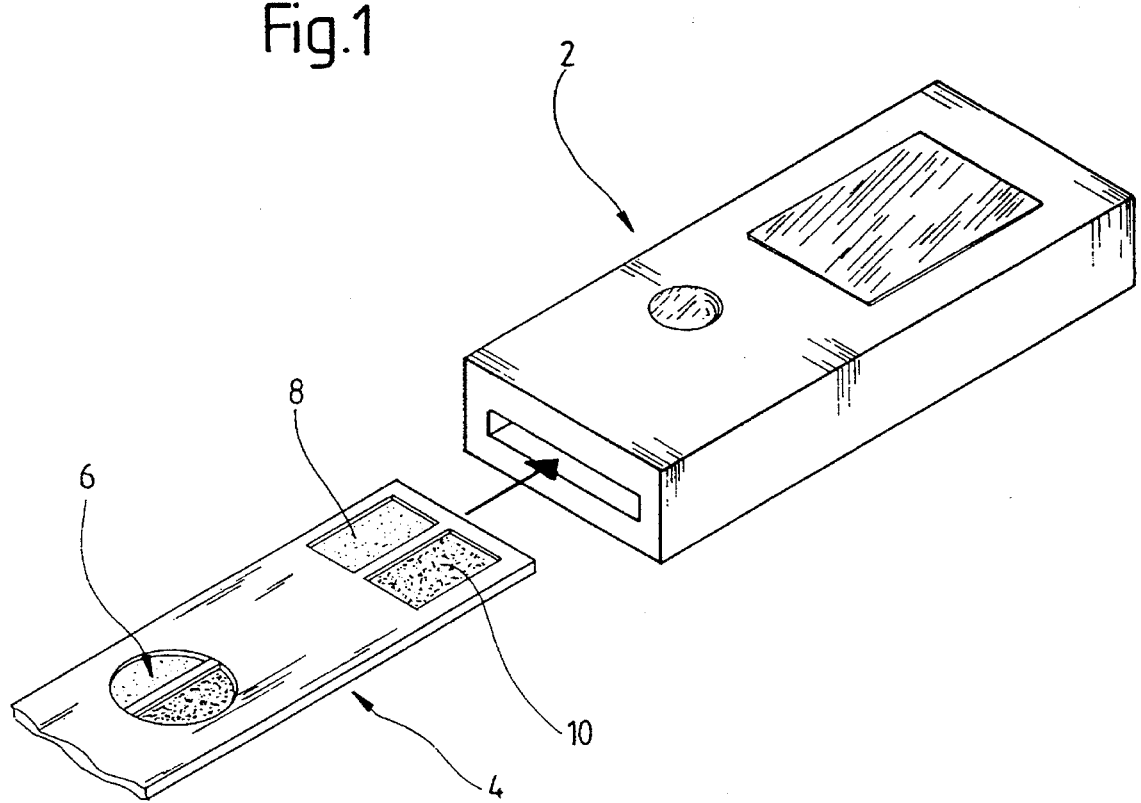
FIG. 1, already described, shows in perspective a general view of a measuring device and a removable sensor with which it is used.
Figure 2:
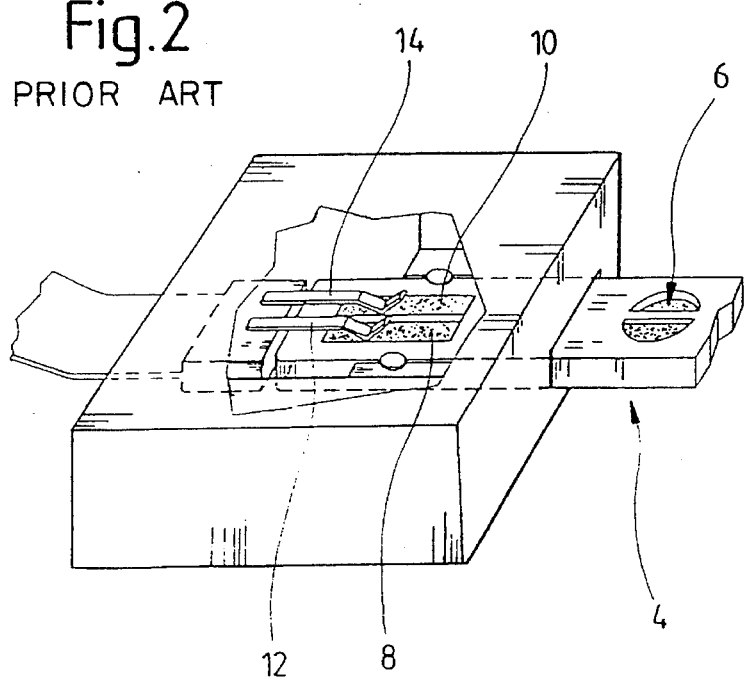
FIG. 2, already described, is a partial view of a measuring device of the prior art schematically showing the electrical connection between the measuring device and a removable sensor with which it is used.
Figure 3:
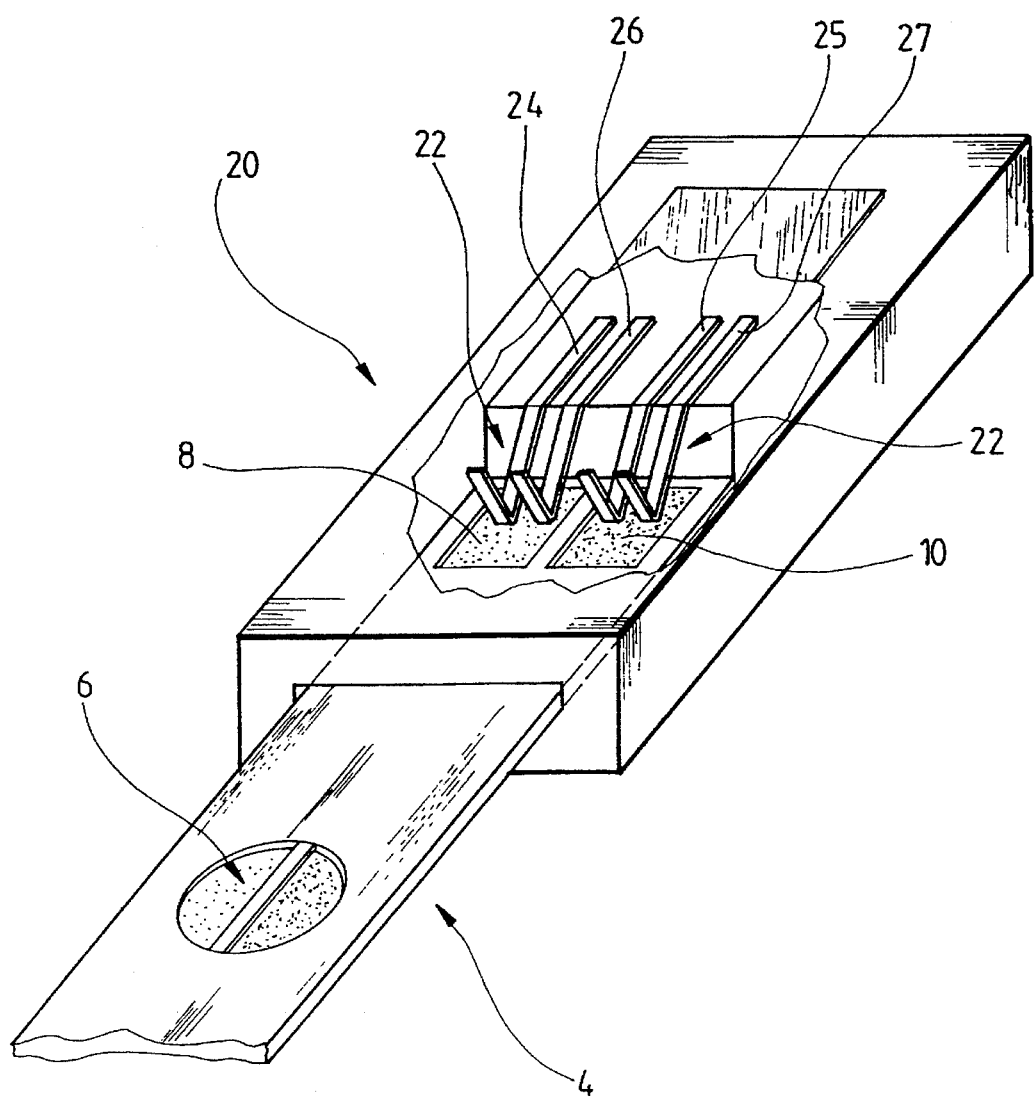
FIG. 3 shows in perspective a schematic view of a measuring device according to the invention used with a removable sensor.

In FIG. 3, the measuring device according to the invention, designated by the general reference 20, is used with a removable sensor 4 comprising at least an active zone 6 and two electrical contact surfaces 8 and 10. These electrical contact surfaces 8 and 10 are electrically insulated from each other and are electrically connected to active zone 6 by means of two respective conductors (not shown) integrated into removable sensor 4.

Measuring device 20 includes connection means 22 formed by four electrical contacts 24, 25, 26 and 27, consisting respectively of four metallic strips or wires. These four metallic strips 24 to 27, used as electrical contact means between measuring device 20 and removable sensor 4, are bent and exhibit a certain elasticity enabling them to rest on electrical contact surfaces 8 and 10 of removable sensor 4, that is to say, to exercise a certain contact pressure on said electrical contact surfaces 8 and 10.

Thus, each of two electrical contact surfaces 8 and 10 is used with two electrical contacts 24 and 26, 25 and 27, independent of each other. This doubling of electrical contacts by electrical contact surface enables the electrical connection between removable sensor 4 and measuring device 20 to be tested by means of an electric or electronic circuit arranged in said measuring device. Two embodiments of this electric circuit of measuring device 20 according to the invention will be described below.

Figure 4:
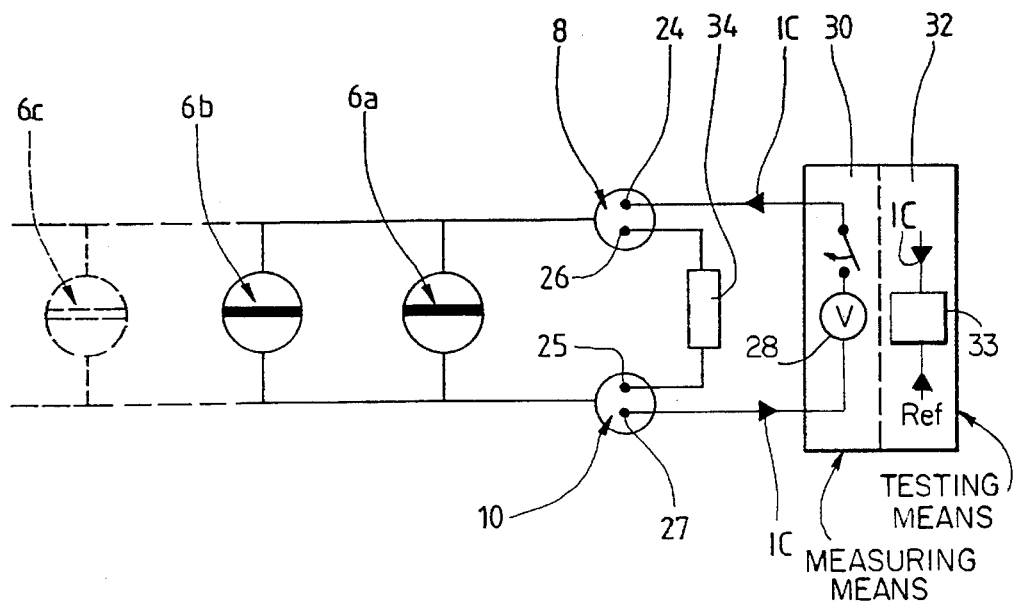
FIG. 4 shows a schematic view of a first embodiment of the electric circuit of the measuring device according to the invention.

In FIG. 4 a first embodiment of the electric circuit of a measuring device according to the invention is shown.

FIG. 4 shows a schematic diagram of two electrical contact surfaces 8 and 10 of a removable sensor and the four electrical contacts 24, 25, 26 and 27 of a measuring device according to the invention which are used with them.

It should be noted here that the removable sensor is a multiple zone sensor comprising a plurality of active zones 6a, 6b, 6c, electrically connected in parallel to two electrical contact surfaces 8 and 10, there being any number of these actives zones. The electric circuit of the measuring device according to the invention comprises measuring means 30 and testing means comprising a testing electronic unit 32 and testing resistor 34. It will be noted that measuring means 30 and testing electronic unit 32 may be formed by one and the same electronic unit.

Electrical contacts 24 and 27 used respectively with contact surfaces 8 and 10 are connected to measuring means 30. On the other hand, electrical contacts 25 and 26 used respectively with electrical contact surfaces 8 and 10 are connected to testing resistor 34. In this embodiment, the value of the electrical resistance of active zones 6a, 6b and 6c, when these active zones are not in contact with a substance which is electrically conductive in conjunction with one of said active zones, is very high, more particularly almost infinite.

In order to be able to test whether the electrical connections between electrical contact 24 and contact surface 8 and between electrical contact 27 and contact surface 10 are correctly established, electrical contacts 24 and 27 are capable of being electrically connected to a voltage source 28 which is part of measuring means 30 and/or testing electronic unit 32. It is envisaged that testing resistor 34 has a value enabling an electric test current IC to be established when electrical contacts 24 and 27 are connected to said voltage supply. Testing resistor 34 has, for example, a value of the order of several tens of $K\Omega$, in particular 30 $K\Omega$.

It is advantageous for the voltage source used to establish an electric test current IC to be a constant voltage supply. Thus, knowing the value of testing resistor 34, it is possible to determine the minimal value of an electric test current IC required to flow through testing resistor 34 when the electrical connection between four electrical contacts 24, 25, 26 and 27 and two electrical contact surfaces 8 and 10 is correctly established.

In order to test whether said minimal value is achieve during a testing phase, namely a phase in which active zones 6a, 6b and 6c are not in contact with any substance which is electrically conductive in conjunction with one of the active zones, testing means 32 comprises means for comparing (33) the value of electric test current IC to a first reference value Ref. approximately equal to said minimal value.

In an alternative of this first embodiment, test current IC may be stored, the value of this test current IC being taken into consideration by measuring means 30 at the time of measuring a substance to be analysed by means of at least one of active zones 6a, 6b and 6c of the removable sensor used with the measuring device according to this first embodiment of the invention.

It will also be noted that the resistance of testing resistor 34, electrically connected in parallel with active zones 6a, 6b and 6c to measuring means 30, is to be taken into consideration in the arrangement of measuring means 30. For the sensitivity of the measuring device arranged according to this first embodiment to be high, it is preferable that the electrical resistance of each of active zones 6a, 6b and 6c, when placed in contact with a substance to be analysed, has a value less than the value of testing resistor 34, for example, ten times smaller.

In another alternative of this first embodiment, said means for comparing also enables the value of test current IC to be compared to a second reference value. The removable sensor used with the measuring device according to this alternative, is considered to be defective when the value of test current IC is greater than this second reference value. This comparison notably enables a defect in one of active zones 6a, 6b or 6c or a short-circuit intervening in the removable sensor to be detected.

Thus, during a testing phase prior to a measurement, the measuring device used with a removable sensor is judged to be in a correct operating condition when the value of test current IC is included between the first reference value and the second reference value. To this end, the testing means of the measuring device according to the invention is arranged to indicate that this measuring device used with a removable sensor introduced into the latter is not functioning when the value of the test current is less than said first reference value or greater than said second reference value.

Figure 5:
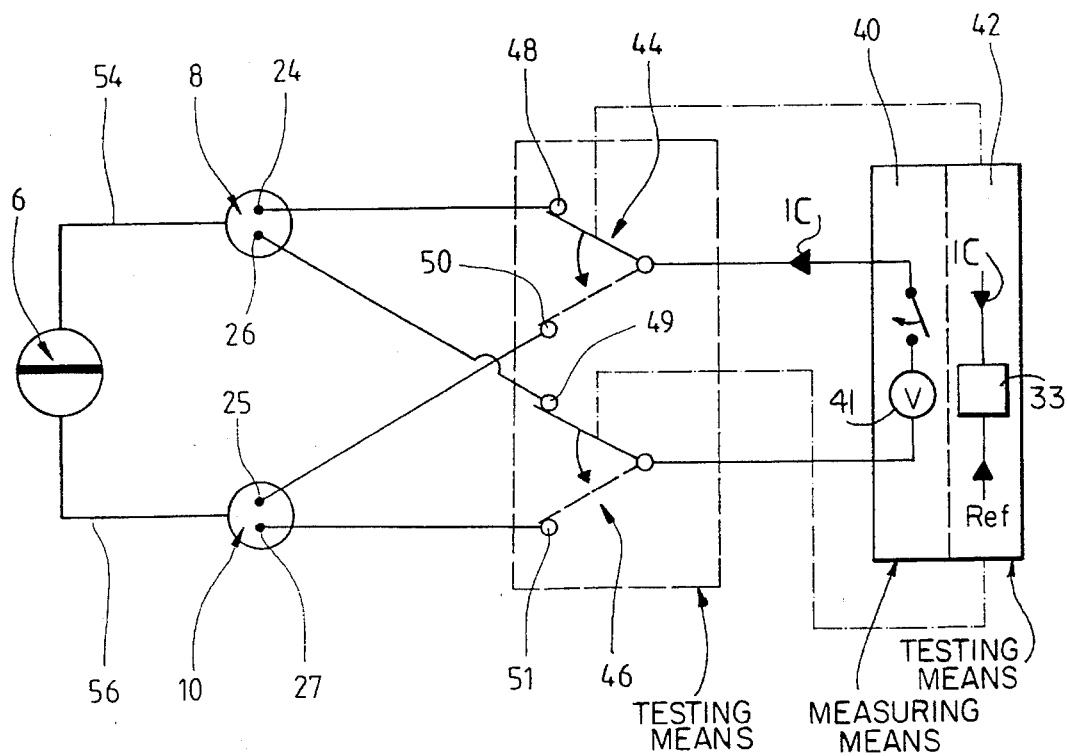
FIG. 5 shows a schematic view of a second embodiment of the electric circuit of the measuring device according to the invention.

Referring to FIG. 5, a second embodiment of the electric circuit of a measuring device according to the invention will be described below.

In FIG. 5 two electrical contact surfaces 8 and 10 of a removable sensor and active zone 6 of this removable sensor are also shown.

Each of two electrical contact surfaces 8 and 10 is also used with two electrical contacts 24 and 26, 25 and 27 belonging to the measuring device. This measuring device also comprises measuring means 40 and testing means comprising a testing electronic unit 42 and two switches 44 and 46. Each of two switches 44 and 46 may be actuated independently of each other by testing electronic unit 42. The two switches 44 and 46 are electrically connected to measuring means 40, each of these two switches 44 and 46 being capable of switching between a first terminal 48, 49 and a second terminal 50, 51.

The two terminals 48 and 50 of switch 44 are connected respectively to electrical contacts 24 and 25, which are respectively used with the two electrical contact surfaces 8 and 10 of the removable sensor. Similarly, the two terminals 49 and 51 of switch 46 are respectively connected to the two electrical contacts 26 and 27, which are respectively used with the two electrical contact surfaces 8 and 10. Measuring means 40 and/or testing electronic unit 42 comprise a voltage source 41 capable of being connected in series to the two switches 44 and 46.

This second embodiment of the invention enables the electrical connection of electrical contacts 24 and 26 used with contact surface 8 and the electrical connection of electrical contacts 25 and 27 used with electrical contact surface 10 to be checked separately.

When switches 44 and 46 are connected respectively to terminals 48 and 49, it is possible to test whether an electric test current IC flows between electrical contacts 24 and 26 when the two switches 44 and 46 are connected in series to said voltage source. Similarly, when the two switches 44 and 46 are connected respectively to terminals 50 and 51, it is possible to test whether the electrical connection between electrical contacts 25 and 27 and electrical contact surface 10 is correctly established.

Thus, it is possible to test independently the state of the electrical connections of each of the two electrical contact surfaces 8 and 10. Further, this second embodiment of the invention enables the electrical connection between the removable sensor and the measuring device to be tested without the resistance of active zone 6 to the passage of an electric current or the state of active zone 6 having an effect on the test carried out.

Also, testing electronic unit 42 comprises means for comparing 33 enabling the value of an electric test current flowing either between electrical contacts 24 and 26, or between electrical contacts 25 and 27 to be compared to a first reference value Ref. corresponding to a minimal current below which the electrical connection is considered to be incorrectly established.

This second embodiment also enables the state of active zone 6 to be tested by switching switch 44 onto terminal 48 and switch 46 onto terminal 51 or by switching switch 44 onto terminal 50 and switch 46 onto terminal 49. It is thus possible to test that the resistance of active zone 6 of the removable sensor to the flow of an electric current, when active zone 6 is not in contact with any substance which is electrically conductive in conjunction with this active zone, is not less than a determined value.

To achieve the latter test, comparing means of testing electronic unit 42 enables the value of an electric test current capable of flowing through active zone 6 to be compared to a second reference value. When the latter electric control current has a value less than this second reference value, the removable sensor is considered to be defective. This defectiveness may arise, for example, from the active zone itself or from a short-circuit between the two conductors 54 and 56 electrically connecting active zone 6 to contact surfaces 8 and 10.

Finally, it will be noted that the second embodiment of the invention is also suitable for multiple zone removable sensors, just as the first embodiment described in FIG. 4 is suitable for single-zone removable sensors.

What is claimed is:

1. A measuring device for use with a removable sensor, said sensor having at least an active zone for sensing a physical or chemical parameter, and having at least two electrical contact surfaces electrically connected to said active zone, said measuring device having a normal mode and a test mode, and comprising:

an electric measuring circuit for measuring, in said normal mode, said physical or chemical parameter based on said sensing of said active zone;

a connection comprising at least two first contacts, each of said first contacts establishing a respective electric connection between said two electrical contact surfaces of said removable sensor and said electric measuring circuit;

a testing unit for testing said electric connection between said two electrical contact surfaces of said removable sensor and said electric measuring circuit; and said connection also comprising at least two second contacts, each of said second contacts:

a) establishing a respective electric connection between said two electrical contact surfaces of said removable sensor and said testing unit, and b) enabling an electric test current to flow, in said test mode, between any one of said two first contacts and a respective one of said second contacts which is associated with an identical one of said two electrical contact surfaces.

2. The measuring device according to claim 1, wherein:

one of said electric circuit and said testing unit comprises a voltage source electrically connected, in said test mode, in series to said two first contacts;

said testing unit includes an electric testing resistor electrically connected in series with said two second contacts;

said voltage source and said electric testing resistor causing said electric test current to flow between said two first contacts in said test mode;

said electric test current is measured by said electric measuring circuit to produce a value of said electric test current;

said testing unit also includes a comparator for enabling said value of said electric test current to be compared to a first reference value; and said testing unit is arranged to indicate a malfunction when said value of said electric test current is less than said first reference value.

3. The measuring device according to claim 2, wherein:

said active zone of said removable sensor has a high resistance to the flow of an electric current between said two electrical contact surfaces when said active zone is not in contact with any substance which is electrically conductive in conjunction with said active zone;

said comparator also enables the value of said electric test current to be compared to a second reference value;

said testing unit is arranged to indicate a malfunction when said value of said electric test current is greater than said second reference value.

4. The measuring device according to claim 1, wherein said measuring device and said removable sensor are arranged to measure glucose levels in blood.

5. A measuring device for use with a removable sensor, said sensor having at least an active zone for sensing a physical or chemical parameter, and having at least two electrical contact surfaces electrically connected to said active zone, said measuring device having a normal mode and a test mode, and comprising:

electric measuring means for measuring said physical or chemical parameter based on said sensing of said active zone;

connecting means comprising at least two first contact means, each of which establishes a portion of a respective electric connection between said two electrical contact surfaces of said removable sensor and said electric measuring means;

testing means for testing said electric connection between said two electrical contact surfaces of said removable sensor and said electric measuring means;

said connecting means also comprising at least two second contact means, each of which:

a) establishes a respective electric connection between said two electrical contact surfaces of said removable sensor and said testing means, and b) enables an electric test current to flow between any one of said two first contact means and a respective one of said second contact means which is associated with an identical one of said two electrical contact surfaces;

said testing means comprising:
 a first switch, capable of switching between a first terminal and a second terminal, and
 a second switch capable of switching between a third terminal and a fourth terminal;

said first and said second switch being connected to said electric measurement means;

said first and third terminals being respectively connected to said two first contact means;

said second and fourth terminals being respectively connected to said two second contact means;

one of said measuring means and said testing means including a voltage supply electrically connected, in said test mode, in series to said first and said second switch;

said testing means activating said first and said second switch independently to connect one of said two first contact means and said respective one of said two second contact means with said electric measuring means, thereby enabling said electric test current to flow through said one of said two first and said respective one of said two second contact means;

said testing means also including comparing means for enabling said value of said electric test current to be compared to a first reference value; and said testing means being arranged to indicate a malfunction when said value of said electric test current is less than said first reference value.

6. The measuring device according to claim 5, wherein:

said active zone of said removable sensor has a high resistance to the flow of an electric current between said two electrical contact surfaces when said active zone is not in contact with any substance which is electrically conductive in conjunction with said active zone;

said comparing means also enables the value of said electric test current to be compared to a second reference value;

said testing means is arranged to indicate a malfunction when said value of said electric test current is greater than said second reference value.

7. The measuring device according to claim 5, wherein said measuring device and said removable sensor are arranged to measure glucose levels in blood.

8. A measuring device for use with a removable sensor having an active zone for sensing a physical or chemical parameter of a substance, said active zone being electrically connected to electrical contact surfaces, said measuring device having a normal mode and a test mode, and comprising:
 a measuring circuit for electrically measuring (1) in said normal mode, said physical or chemical parameter based on said sensing of said active zone, and (2) in said test mode, an electrical test current;
 a connection for connecting said electrical contact surfaces with said measuring circuit when said removable sensor operably engages said measuring device; and
 a tester using said electrical test current to test a connection between one of said electrical contact surfaces and said measuring circuit.

9. The measuring device as set forth in claim 8, wherein:

said connection includes a pair of first contacts and a pair of second contacts;

said testing unit includes an electric testing resistor;

each of said first contacts couples a respective one of said electrical contact surfaces with said measuring circuit;

each of said second contacts couples a respective one of said electrical contact surfaces with an electric testing resistor of said testing unit;

in said test mode, a voltage source is connected in series with each of said first contacts to create said electrical test current;

said testing unit tests said connection using said electrical test current;

said electrical test current flows through one of said two first contacts and one of said two second contacts;

said one of said two first contacts and said one of said two second contacts have an identical respective one of said electrical contact surfaces; and said testing unit includes a comparator for comparing a value of said electric test current with a preselected first reference value, and indicates when said value of said electric test current is less than said first reference value.

10. The measuring device according to claim 9, wherein:

an electrical resistance across said active zone of said removable sensor is high when not in contact with said substance; and said comparator compares said value of said electric test current with a preselected second reference value, and said testing unit indicates when said value of said electric test current is greater than said second reference value.

11. The measuring device according to 8, wherein:

said testing unit includes two switches, each of which is connected to said measuring circuit;

each of said two switches is switchably connected to either a first or a second one of said electrical contact surfaces via said connection; and in said test mode:
 said two switches are switched to connect to an identical one of said electrical contact surfaces, and a voltage source is connected in series with said two switches to form a path for said electrical test current,
 said testing unit includes a comparator for comparing said value of said electric test current with a preselected first reference value, and
 said testing unit is operable for indicating when said value of said electric test current is less than said first reference value.

12. The measuring device according to claim 11, wherein:

an electrical resistance across said active zone of said removable sensor is high when not in contact with an electrically conductive substance; and said comparator compares said value of said electric test current with a preselected second reference value, and said testing unit indicates when said value of said electric test current is greater than said second reference value.

13. The measuring device according to claim 8, wherein said measuring device, in said normal mode and with said removable sensor operably engaged, measures glucose levels in blood.

* * * * *